US006833359B1

(12) United States Patent
Lazarovits

(10) Patent No.: US 6,833,359 B1
(45) Date of Patent: Dec. 21, 2004

(54) METHOD FOR TREATING SOIL FOR THE CONTROL OF SOIL BORNE PLANT PATHOGENS

(75) Inventor: George Lazarovits, Ontario (CA)

(73) Assignee: Earth Alive Resources Inc., Quebec (CA)

( * ) Notice: Subject to any disclaimer, the term of this patent is extended or adjusted under 35 U.S.C. 154(b) by 0 days.

(21) Appl. No.: 09/646,160

(22) PCT Filed: Mar. 9, 1999

(86) PCT No.: PCT/CA99/00206

§ 371 (c)(1), (2), (4) Date: May 11, 2001

(87) PCT Pub. No.: WO99/45782

PCT Pub. Date: Sep. 16, 1999

Related U.S. Application Data

(63) Continuation-in-part of application No. 09/041,290, filed on Mar. 12, 1998, now abandoned.

(51) Int. Cl.$^7$ ........................ A01N 63/00; A01N 61/00; A01N 41/104

(52) U.S. Cl. ........................... 514/22; 514/54; 514/553; 514/709; 514/710; 514/711; 424/725; 504/101; 504/103; 504/113; 71/11; 71/23; 71/24; 71/25; 71/26; 71/64.01

(58) Field of Search ........................... 514/22, 54, 553, 514/709, 710, 711; 424/725; 504/101, 103, 113; 71/11, 23–26, 64.01

(56) References Cited

PUBLICATIONS

Derwent abstract, accession No. 1995–312015, abstracting: DE 4,404,880, (Aug. 1995).*

* cited by examiner

*Primary Examiner*—John Pak
(74) *Attorney, Agent, or Firm*—Eric Fincham

(57) ABSTRACT

A method for reducing bacterial and fungal soil pathogens which comprises applying to a soil a chemically effective amount of a lignosulfonate, the amount preferably being between 0.05% and about 5% on a volume/weight basis. The method is effective in controlling a number of soil pathogens and can be used to treat the soil for diseases such as potato scab disease.

9 Claims, 13 Drawing Sheets

Effect of ALS and EarthAlive on Nematode Population

Effect of ALS and EarthAlive on Nematode Population

METHOD FOR TREATING SOIL FOR THE CONTROL OF SOIL BORNE PLANT PATHOGENS

This application is a 371 PCT/CA99/00206, filed on Mar. 9, 1999, and a CIP of U.S. application Ser. No. 09/041,290, filed on Mar. 12, 1998, now abandoned.

BACKGROUND OF THE INVENTION

The present invention relates to the field of agriculture and more particularly, relates to a method of treating soil.

The treatment of soil for agriculture purposes is done for many different purposes. Thus, a soil treatment can include the application of many different agents for various purposes ranging from the addition of fertilizers to treating the soil to remove pathogens as well as to increase soil bacteria populations. The control of pathogens in the soil is an issue which has always been of importance and has increasingly become of greater importance due to current methods employed. Thus, the most widely accepted means of treating soil is the use of methyl bromide. However, methyl bromide has been recognized as an ozone depleting chemical and as such, International Agreement has stated that all production in developed countries must be phased out by the year 2005.

Alternatives to methyl bromide do not readily exist and this poses a substantial problem to agricultural producers. Estimates of a cost of over 1 billion dollars annually have been made as a potential future crop damage resulting from the removal of methyl bromide from the market for soil fumigation. Many agriculture products widely produced on a large scale such as potatoes, tomatoes, peppers; strawberries, etc. are susceptible to soil borne pathogens.

Other products for treating soil do exist but have not gained wide acceptance. There are also natural methods for treating the soil including crop rotation and field fallowing. However, these approaches provide a substantially lower return to the agricultural user.

SUMMARY OF THE INVENTION

It is therefore an object of the present invention to provide a method for the treatment of soil which is effective to control some bacterial and fungal soil pathogens.

According to one aspect of the present invention, a method is provided for reducing bacterial and flail soil pathogens comprising the step of applying to a locus to be treated a chemically effective amount of a lignosulfonate.

In a flier aspect of the present invention, there is provided a method of enhancing the characteristics of a soil having bacterial and fungal pathogens therein, the method comprising the steps of mixing ammonium lignosulfonate, at least one agriculturally desirable microorganism, and a food material for the microorganisms, allowing the microorganisms to multiply for a period of time sufficient for the microorganisms to have a concentration of at least one hundred million bacteria per milliliter, and subsequently applying to the soil a chemically effective amount of the mixture.

In a further aspect of the present invention, there is provided a method of treating potato scab disease caused by bacteria Streptomyces comprising the step of applying to a soil containing the bacteria Streptomyces ammonium lignosulfonate in an amount of between 0.05% and 5% on a volume/weight basis and incorporating the ammonium lignosulfonate in the soil.

In a further aspect of the present invention, there is provided a method of controlling at least one soil pathogen selected from the group comprising *Verticillium dahliae*, Streptomyces, Phylophthora, Pythium, Rhizoctonia and Sclerotinia comprising the step of applying to a locus containing one of the soil pathogens a chemically effective amount of a lignosulfonate.

Lignins are a natural polymer which are generally produced as a co product of the paper industry, the lignins being separated from the trees by a chemical pulping process. Lignosulfonates (also known as lignin sulfonates and sulfite lignins) are products of sulfite pulping. Other delignifying technologies can use an organic solvent or high pressure steam treatment to remove lignins from plants.

As aforementioned, lignin is a very complex natural polymer, the exact chemical structure not being known. The physical and chemical properties may differ somewhat depending on the extraction technology. Lignosulfonates have typically been used for their dispersing, binding, complexing and emulsifying properties. Lignins have been used for many years and extensive studies have been done to test lignin impact on the environment To date, lignins have been shown to be safe and not harmful to plants, animals and aquatic life when properly manufactured and applied.

Toxicological studies of lignosulfonates using laboratory animals have been conducted at Stanford Research Institute International in California. Lignosulfonates were found to be essentially non-toxic and non-irritating, not mutagenic or genotoxic and can be safely used in animal and human food contact products. Lignosulfonates have been approved for use as constituent in animal feed and various food contact materials and pesticide formulations by the U.S. Food and Drug Administration.

Lignosulfonates have also found use in various compositions used for gels and binders. Thus, lignosulfonates have been proposed as one component of various binding compositions and particularly suitable for the plugging of wells and the like. It is also been suggested in the art that they can be used in combination with other compounds, as a dust control composition for the treatment of fertilizers.

Calcium lignosulfonate has also been shown as suitable for controlling nematodes which are of the animal kingdom. Reference may be had to U.S. Pat. No. 5,696,094 which shows that various nematode species are affected by the use of calcium lignosulfonate. However, there is no teaching therein that soil borne bacterial and fungal pathogens are affected.

It is also known from Chem. Abstr., vol. 88, no. 7, 13 Feb. 1978 Columbus, Ohio, US; abstract no. 49520, LICHKO, R. P. ET AL that the application of ammonium lignosulfonates increase the calcium ion content in certain soils.

It is known from German Patent DE-A44 04 860 that lignosulfonates can be applied to the soil and/or leaves of a plant.

It is also known from Database CROPU Derwent Izfoimation Ltd. Abstract number, 92-85525, A. Khakimov, R. Teshabaeva & R. Sayrsakova that lignin may be used as a substrate for introducing bacteria before sowing cotton.

It has surprisingly been found that lignosulfonates are useful for controlling both bacterial and fungal soil borne pathogens and in addition, by themselves or in combination with other materials, can be useful as a delivery agent for other microorganisms known to be useful for agricultural production.

The mechanism by which soil borne bacterial and fungal pathogens are controlled by lignosulfonates is not understood However, tests have shown that the application of lignosulfonates to a soil medium can have extremely beneficial results.

As a readily commercially available product, reference herein will be made to ammonium lignosulfate with it being understood that other lignosulfonates may be utilized, either alone or in combination.

The concentration of the ammonium lignosulfonate to be applied to the soil may vary. The determination of the amount can be ascertained by one skilled in the art and which amount may vary depending on different parameters. These parameters could include the type of soil, the crop to be grown, any specific bacterial or fungal pathogen to be controlled, time of application, etc. Thus, for example, depending upon the type of crop to be grown and the time when the crop is placed in the soil, the question of phytotoxicity to the crop may or may not be of concern. One could apply a relatively high dosage when the soil will not be planted for a period of time or alternatively, one could utilize a series of applications at relatively low dosages to provide a cumulative effect over a period of time. Generally, an amount of between 0.05% and 5% on a volume/weight basis (product/soil) may be utilized and when it is applied in a single application, it is preferably applied at a volume/weight basis of between 0.1% and 2%.

As mentioned above, the amount of lignosulfonate to be applied will depend upon the specific application. In the preferred embodiments, an amount of at least 0.1% by volume would be employed given that the material is available as a 45% solution (45% solid/55% liquid). The amount would naturally depend on the bacterial and fungal pathogens to be controlled, the economics, etc. In certain instances and as will be seen hereinbelow, ammonium lignosulfonate might have a biocidal impact—i.e. its effectiveness initially increases with increasing amounts and then subsequently decreases and then increases once again. This bimodal impact phenomenon has been reviewed by Schatz, A. Schalscha, E. B. and Schatz, V, 1964. "Soil organic matter as a natural chelating material. Part 2: The occurrence and importance of paradoxical concentration effects in biological systems". Compost Science 5:126–130.

The method of application of the ammonium lignosulfonate to the soil may be selected from any suitable including application as a dust or granular material or application by means of a liquid medium such as water, etc. Generally, a water based application would be preferred.

The ammonium lignosulfonate may be used either alone or in combination with other materials, including biological and chemical pest protectants. In one particularly preferred embodiment, the ammonium lignosulfonate may also be employed as a delivery agent for microorganisms identified to be useful for agricultural production. The benefits of these microorganisms may be as biofertilizers or as biological control agents. A number of such microorganisms are known in the art and could be incorporated in a mixture of the ammonium lignosulfonate and any additional materials. Such microorganisms would include bacteria, including the gram positive Streptomnyces, fungi, algae, and nematodes that attack insect pests. Commonly employed organisms include, Agrobacterium spp., Pseudomonas spp., Bacillus spp., Rhizobium spp., Streptomyces spp., Azospinilum spp., Enterobacter spp., Trichoderma spp., Gliocladium spp., Sporodesmium spp., Pythium spp., Fusarium spp., Verticillium spp., Talaromyces spp., various wood decomposing fingi, etc.

One particular advantageous method comprises combining ammonium lignosulfonate with desired microorganisms and food for the microorganisms and then allowing the microorganisms to grow in the ammonium lignosulfonate for a period of time sufficient to substantially increase in numbers—i.e., at least one billion bacteria per milliliter of mixture. Such a method provides an extremely economical means of delivering the microorganisms to the soil as the mixture can be then diluted to apply one million bacteria per milliliter of water applied to the soil.

A further advantage of the use of a lignosulfonate is the restoration of the soil with the lignins from the lignosulfonate. Thus, many soils have, over a period of years, become depleted of many of the natural elements which were originally present in the soil. The application of the lignins, being a plant material, can act to restore such elements and increase soil health.

Ammonium lignosulfonate has been used in feed products. In particular, one such product is marketed under the trademark "Earth Alive" and is intended for use on house plants. The product contains fertilizer, ammonium lignosulfonate and certain bacteria. This product was tested in conjunction with tests on ammonium lignosulfonate without the additives.

BRIEF DESCRIPTION OF THE DRAWINGS

Reference will now be made to drawings in which.

DESCRIPTION OF THE PREFERRED EMBODIMENTS

Reference will now be made to Examples demonstrating embodiments of the invention.

EXAMPLE 1

Soils used for this Example are from a potato field near Alliston, Ontario. Potatoes grown in this field have had a high incident of verticillium wilt and potato scab. Verticillium wilt is caused by the fungus *Verticillium dahliae* and potato scab is caused by bacteria belonging to genus Streptomyces. Earlier studies (KATAN) have shown that both these pathogens are excellent models for studying the effects of soil amendments on control of diseases caused by soil borne pathogens. In general when the populations of these two organism were controlled so were diseases caused by Phylophthora, Pythium, Rhizocionia, Sclerotinia, various nematode spp etc.

Figure 6:
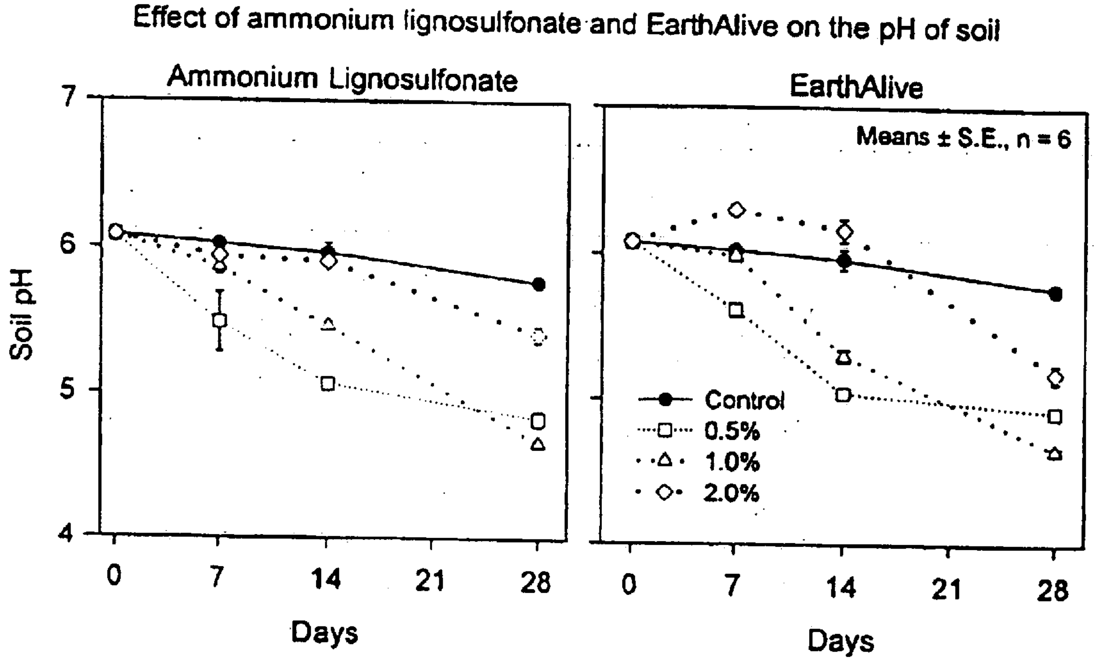
FIG. 6 graphs the effect of ammonium lignosulfonate and Earth Alive™ on the pH of soil.

Soils were mixed with 3 concentration of ammonium lignosulfonate (0.5, 1.0 and 2.0% vol./wt.—i.e. 2 mL ALS/100 g soil (dry wt.)). Twelve test tubes were setup and 3 test tubes were sampled at each of days 7, 14, and 28. Soil pH was measured (FIG. 6). Populations of total fungi total bacteria, total Streptomyces bacteria and pathogenic Streptomyces were determined by plating soil extractions onto selective media. The Verticillium bioassay consisted of sealing the resting structure of the fungus, called microsclerotia (MS=serve a similar function to plant seeds) in nylon mesh bags which were buried in the soil mixtures. The bags were removed at day 7, 14, and 28 and plated out on selective media, and percent germination was determined.

Figure 2:
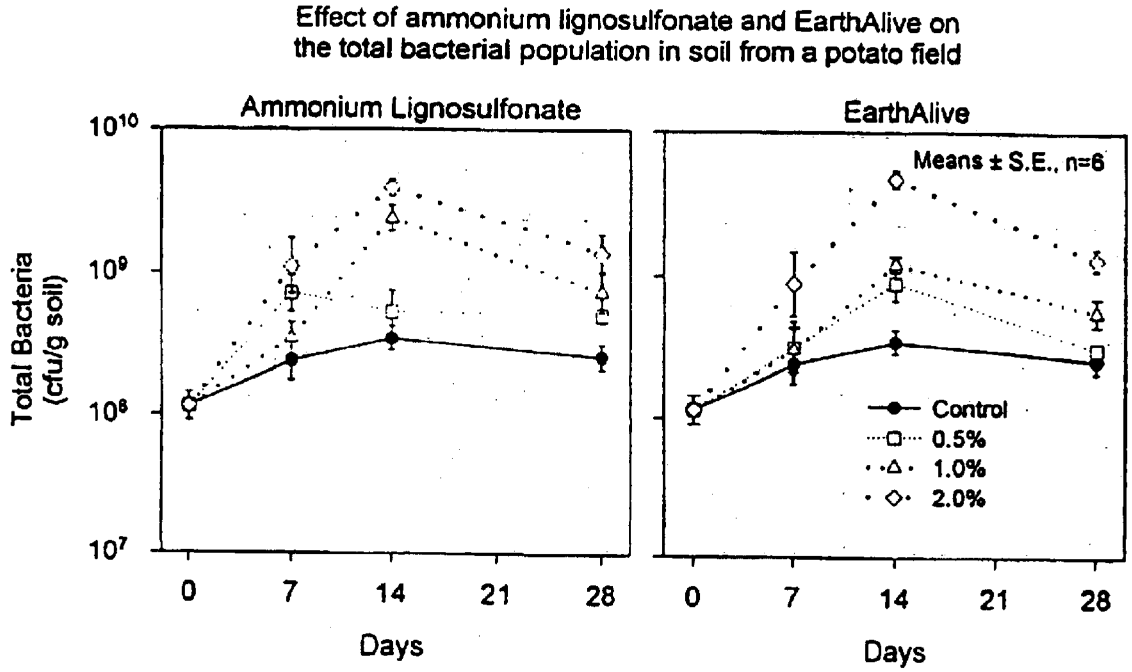
FIG. 2 is a graph illustrating the effect of ammonium lignosulfonate and Earth Alive™ on the total bacterial population in soil from a potato field.

The pH of the soil showed a slight decrease at 0.5 and 1.0% levels. However, the 2% mixture gave a similar pH to that of the control. All concentrations cause an increase in total soil bacterial populations (FIG. 2). In general, within 14 days of incubation, the total bacterial population increased from 300 million to more than 100 billion bacteria/grams of soil. The 2% mixture of ammonium lignosulfonate caused a decrease in pathogenic Streptomyces populations on the selective media. The exact reduction in numbers of pathogenic Streptomyces is difficult to determine as the overall increase in total bacteria makes it impossible to obtain an accurate count. However, a decrease of at least 10 to 100 times in the number of pathogenic Streptomyces at day 14 is apparent. The pathogens were thus reduced to a level below that required to cause disease losses. It is to be noted that there is no control presently available for potato scab and growers lose significant yield due to rejection of the tubers because of poor quality.

Figure 5:
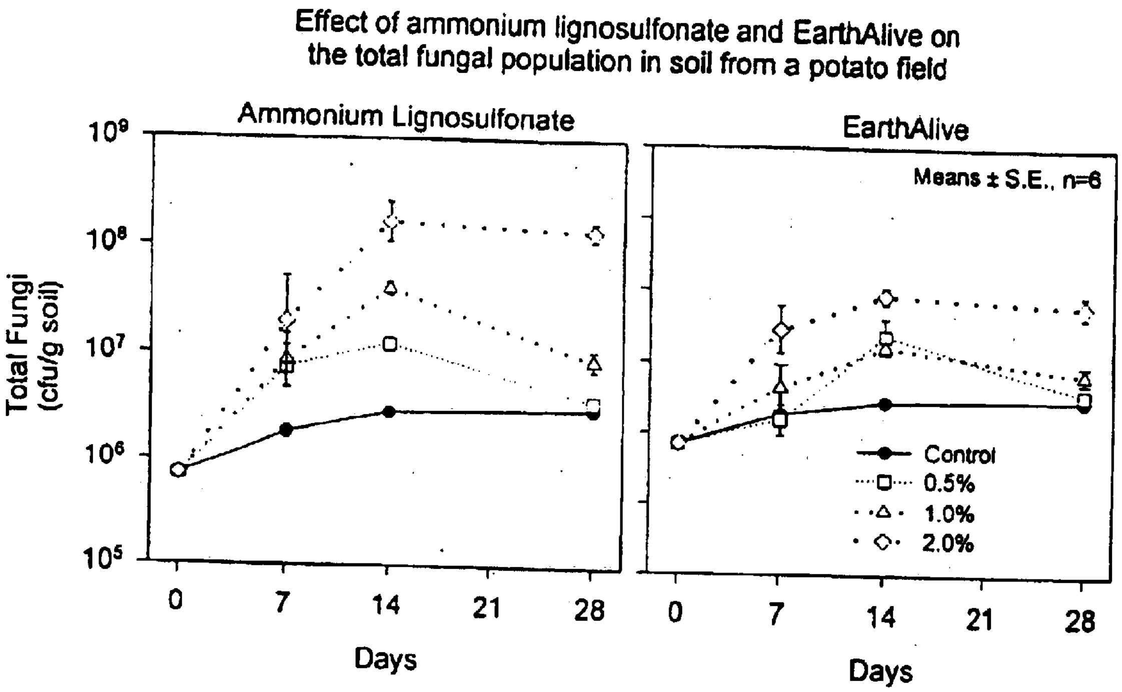
FIG. 5 illustrates graphs showing the effect of ammonium lignosulfonate and Earth Alive™ on the total fungal population in soil from a potato field.

The ammonium lignosulfonate also initially increased the total fungal populations (FIG. 5). There was a linear increase in fungal population as the mixture concentration of ammonium lignosulfonate was increased. At a 2% ammonium lignosulfonate concentration, the fungi populations increased from 2.7 million to 76 million per gram of soil.

Figure 3:
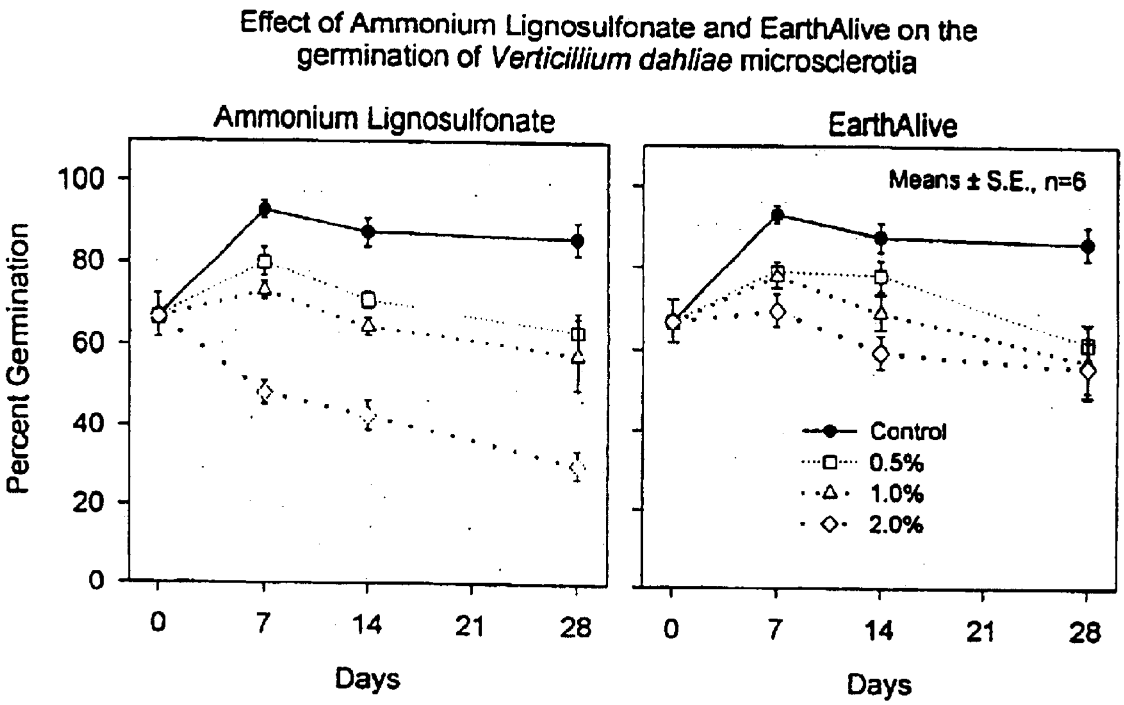
FIG. 3 comprises graphs showing the effect of ammonium lignosulfonate and Earth Alive™ on the germination of *Verticillium dahliae* microsclerotia.
Figure 4:
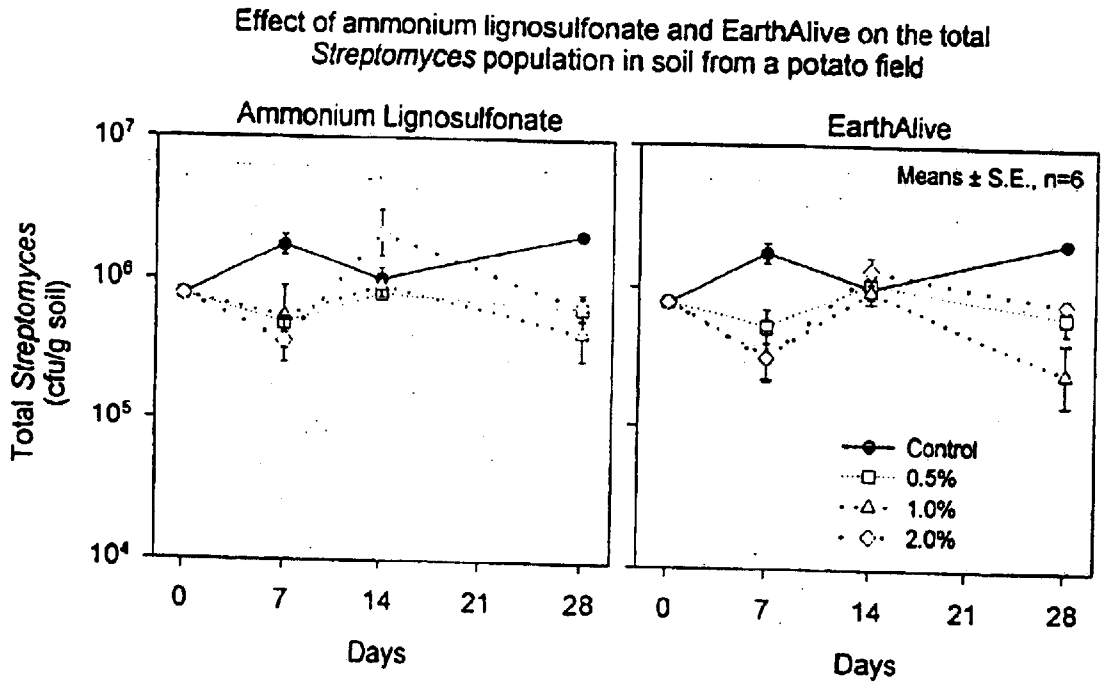
FIG. 4 illustrates graphs showing the effect of ammonium lignosulfonate and Earth Alive™ on the total Streptomyces population in soil from a potato field.

As shown in FIG. 3, all concentrations of the ammonium lignosulfonate decreased the germination of the *V. dahliae* microsclerotia MS. The germination rate decreased with the increase in the mixture concentration of the ammonium lignosulfonate. Soils that were treated with 2% ammonium lignosulfonate reduced microsclerotia germination by over 50% by day 14.

EXAMPLE 2

A product marketed under the trademark "Earth Alive" which is a proprietary product uses ammonia lignosulfonate as a base along with certain microorganisms was tested. The total bacterial was 56 million colony forming units/milliliter.

To the Earth Alive™ product there was added 1% yeast extract, 1% glucose and 10 grams of soil. The suspension was incubated on a rotary shaker for 30 days. This allowed those organisms already present in the Earth Alive™ product and any soil microorganisms that could grow in the ammonium lignosulfonate base to increase in numbers. The population of bacteria after 30 days was 4.3 billion per milliliter versus the original number of 56 million per milliliter., The population levels of microorganisms is of prime importance from the commercial aspect of delivering the microorganisms to commercial fields. Assuming that 1 million bacteria per milliliter are adequate to bring about effective biological control in a commercial soil, then a product prepared using the enriched medium could be diluted 1:1000 to saturate an agricultural soil with 1.2 centimeters of water per acre, 74 thousand liters of water have to be applied and therefore only 54 liters of a product with a billion bacteria per milliliter are required.

Figure 1:
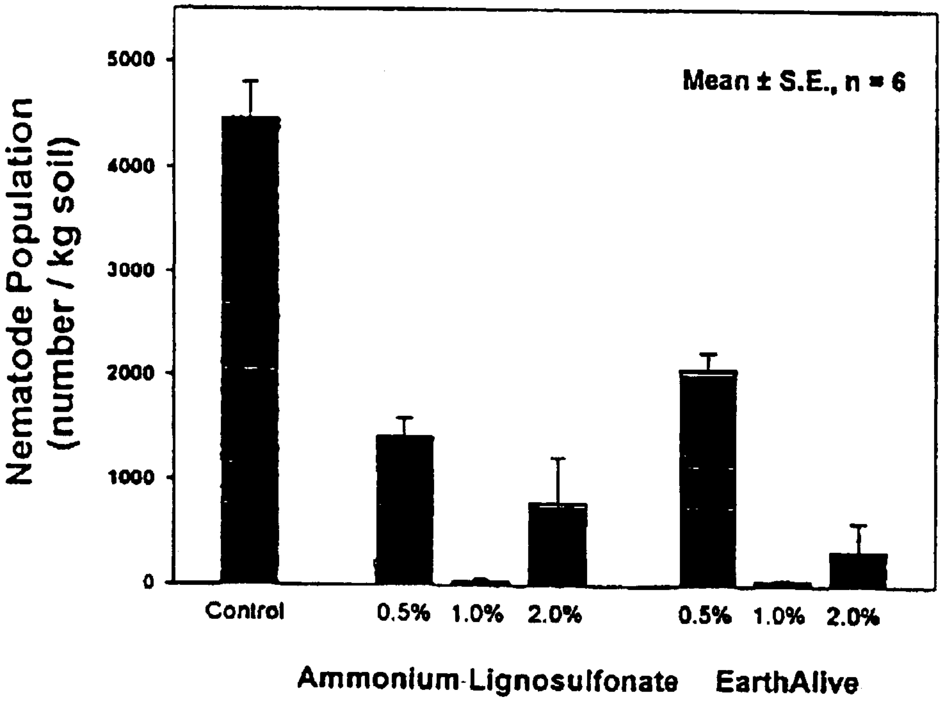
FIG. 1 is a graph illustrating the effect of ammonium lignosulfonate (ALS) and the product Earth Alive™ on nematode population.

In both of the above examples, the effect of ammonium lignosulfonate and Earth Alive™ on the nematode population was significant (FIG. 1). As will be seen from FIG. 1, the ammonium lignosulfonate and Earth Alive™ has a bimodal impact decreasing the total population at a 1% concentration while there is a subsequent increase.

EXAMPLE 3

An experimental plot was set up on a commercial potato farm near Delhi, Ontario in May 1998. The quantities of ammonium lignosulfonate applied are listed in Table 1. Three replicate plots/treatment in a randomized block design were set up. Each plot was 13×25 ft and there was a 10 ft buffer zone between each of the blocks. There was also a 2 ft buffer zone between each plot within a block.

TABLE 1

Amount of Ammonium Lignosulfonate.

| Treatments | Amount/plot[y] | Amount/acre | %/soil (v/w)[z] |
|---|---|---|---|
| 1. Untreated control | | | |
| 2. ALS | 8 gal (US) | 1072 gal | 0.5% |
| 3. ALS | 16 gal | 2144 gal | 1.0% |

[y]Three replicate plots (13 × 25 ft)/treatment
[z]Based on the assumption that 1 $ft^2$ to a depth of 6 inches contains about 40 lbs of soil.

Ammonium lignosulfonate was applied over the soil surface by watering cans and the plots rototilled with a commercial farm rototiller to a depth of 6 inches. Weed emergence in the plots was determined four weeks later. Fertilizer (nitrogen; 10.2%, potassium; 6.6%, phosphorous; 14.6%, calcium; 4.0%, magnesium; 3.2%, and zinc; 0.5%) at a rate of 1200 lbs/acre was broadcast by hand on all plots. The plots were then cultivated twice and potato tubers cv. Yukon Gold planted by the grower (4 rows of 25 plants/row). Some of the treatment were phytotoxic to the potato plants and these plots were replanted 4 weeks later. The plots were treated the same in all other ways. Soil samples were taken at 0, 8, 14 and 20 weeks after amendment incorporation. About 20 soil cores to a depth of 6 inches were taken with a soil corer from each plot and mixed together. The effects of amendments on soil pH, ion concentration, and microbial populations were determined as described below. Bags containing *V. dahliae* resting structures (microsclerotia; MS) were attached to plastic stakes and buried in soil (2 bags/plot) immediately after application of amendments. Two bags/plot were removed after 4 weeks and analyzed as described below. Incidence of Verticillium wilt and potato scab were determined as described below. Tubers were harvested in the fall from the middle two rows of each plot and the yield determined. The rest of the tubers were harvested and discarded and the grower cultivated the plots along with the rest of the field.

Soil Microbial Enumeration and pH Analysis

The soil microbial population was determined for all treatments by adding 10 g of soil to 90 mL of sterile water agar (0.1% w/v) in a plastic pouch (17×30 cm). The pouches were heat sealed and shaken on an orbital shaker (200 rpm) for 2 h. The soil mixtures were then homogenized by placing the pouches in a Stomacher blender set on normal speed for 30 s. Serial 10-fold dilutions were prepared in saline solution (0.85% NaCl) and plated onto three media which were incubated at room temperature (22° C.). The number of culturable Streptomyces bacteria was counted on Streptomyces Selective Medium (Conn et al. 1998) after 14 days, the non-filamentous bacteria counted on Pseudomonas-Agar F (PAF) medium after 7 days, and the number of fluorescent and Gram-negative bacteria counted on PAF medium (plus penicillin G, 0.2 g/L) after 3 and 7 days, respectively. Numbers of microorganisms were adjusted to represent colony forming units (CFU)/g dry soil. Soil pH was determined by measuring the pH of soil-water agar mixtures.

Verticillium Assay

After bags of *V. dahliae* were removed from soil, the contents were plated onto a semi-selective medium (Hawke & Lazarovits 1994) using an Anderson air sampler. Plates were incubated at 25° C. in the dark for 2 weeks. Fungal colonies growing out of MS, characteristics of *V. dahliae*, were counted to determine the percent germination of MS.

Soil DNA Extraction

Soil DNA extraction for week 20 samples was carried out according to Borneman el al. (1996) using Bio101 FastDNA SPIN kit for soil with following modifications: after the FastPrep machine treatment, 700 μl of supernatant was removed and mixed with 250 μl protein precipitation solution (i). This mixture was centrifuged at 16000×g for 5 min at room temperature. The supernatant was then transferred and mixed with the binding matrix in a new Eppendorf tube. This tube was gently inverted for 2 min. placed a rack for 3 min to allow the settling of the binding matrix, and the mixture was transferred to a Spinfilter and centrifuged for 1 min at 16000×g. The pellet in the Spinfilter was washed twice with 500 μl wash solution (SEWS-M) and centrifuged for 2 min to dry the pellet. The DNA was eluted by transferring the Spinfilter to a new catch tube, adding 100 μl elution solution (DES), and then centrifuged for 1 min at 16000×g. The eluted DNA was diluted 10 fold with TE for polymerase chain reaction (PCR).

PCR Reaction

The two primers used were 5'GCGCCATATGAGCGCGAACGGAAGCCCCGGA 3'(N2) and 5'GCGCGAATTCGCAGGTCGTCACGAAGGATCG 3'(N3) according to Bukhalid et al. (1997). For each 25 μl PCR reaction, there were 5 μl 5× Gitschier buffer (Kogan et al., 1987), 0.2 μl BSA, 1.15 μl $H_2O$, 1.25 μl DNTPs mix (25 mM ATP:GTP:CTP:TTP, 1:1:1:1:1), 2 μl DMSO, 1 μl of primer N2 (50 pmol/μl), 1 μl of primer N3'(50 pmol/μl), 0.4 μl of Taq polymerase (2U Perkin/Elmer) and 2 μl soil DNA extract. The PCR reaction was carried out on a GeneAmp 9600 with the following conditions: denaturing at 96° C. for 1 min, annealing at 65° C. for 1 min, and polymerizing at 72° C. for 8 min for 55 cycles. For each soil DNA sample, three PCRs including one with just the soil DNA, one with the putative pathogen DNA added, and one with the competitive DNA added as internal standard were done.

DNA Quantification

The quantification of the amplified DNA was done by visualizing and rating by naked eyes (with 0 representing no signal, 1 low signal, 2 medium high signal, and 3 high signal) the intensity of the band of the expected size, and the intensity ratio of the expected band to that of the internal standard on a 1.5% agarose gel running for 2 h at 80 Volts.

Disease Assessment

Incidence of *V. dahliae* was determined by collecting a leaf petiole from the lower portion of each of 25 potato plants in the middle two rows of each plot in mid-August. The petioles were surface sterilized by placing them in 1.5% sodium hypochlorite for 2 min. Three sections from each petiole were plated onto a semi-selective medium (Hawke & Lazarovits 1994), the plates incubated at 25° C. in the dark for 2 weeks, and the presence or absence of *V. dahliae* determined microscopically. A plant was scored as infected if *V. dahliae* was present in just one petiole section.

The severity of potato scab was evaluated using a rating scale of 0 to 6 based on the percentage of tuber surface covered with scab lesions where 0=0%, 1=trace to 5%, 2=6–15%, 3=16–25%, 4=26–35%, 5=b 36–60%, and 6=61–100%. One hundred tubers from each of the three replicates/treatment were evaluated. Each tuber was examined and placed in one of the seven classes with the aid of disease assessment keys showing percent surface areas covered with lesions (Conn et al. 1990, Weinhold et al. 1964).

TABLE 2

Effect of Ammonium Lignosulfonate (ALS) on microbial populations in a commercial potato field

| Treatment | Weeks after application 0 | 8 | 14 | 20 |
|---|---|---|---|---|
| | Total bacterial population (× $10^6$ CFU/g soil) | | | |
| Control | 24 ± 5.4 | 38 ± 3.6 | 30 ± 8 | 120 ± 13 |
| 0.5% ALS | 24 ± 5.4 | 320 ± 98 | 37 ± 12 | 26 ± 4 |
| 1.0% ALS | 24 ± 5.4 | 140 ± 13 | 18 ± 7 | 180 ± 52 |
| | Total Gram-negative bacterial population (× $10^4$ CFU/g soil) | | | |
| Control | 19 ± 8.2 | 6.8 ± 1.5 | 13 ± 5.2 | 57 ± 9.5 |
| 0.5% ALS | 19 ± 8.2 | 72 ± 33 | 120 ± 51 | 62 ± 18 |
| 1.0% ALS | 19 ± 8.2 | 590 ± 45 | 330 ± 50 | 56 ± 19 |
| | Total Gram-positive bacterial population (× $10^6$ CFU/g soil) | | | |
| Control | 24 ± 5.4 | 38 ± 3.6 | 30 ± 7.8 | 120 ± 13 |
| 0.5% ALS | 24 ± 5.4 | 320 ± 98 | 36 ± 12 | 26 ± 4 |
| 1.0% ALS | 24 ± 5.4 | 140 ± 13 | 150 ± 6.4 | 480 ± 260 |

TABLE 2-continued

Effect of Ammonium Lignosulfonate (ALS) on microbial populations in a commercial potato field

| Treatment | Weeks after application 0 | 8 | 14 | 20 |
|---|---|---|---|---|
| | Fluorescent bacterial population (CFU/g soil) | | | |
| Control | 2400 ± 790 | 820 ± 97 | 320 ± 220 | 11000 ± 5000 |
| 0.5% ALS | 2400 ± 790 | 90 ± 0 | 570 ± 460 | 6100 ± 3200 |
| 1.0% ALS | 2400 ± 790 | 1500 ± 1400 | 570 ± 470 | 99 ± 0 |
| | Total fungal population (× $10^4$ CFU/g soil) | | | |
| Control | 22 ± 5 | 18 ± 1.5 | 220 ± 61 | 260 ± 36 |
| 0.5% ALS | 22 ± 5 | 72 ± 33 | 1300 ± 58 | 720 ± 85 |
| 1.0% ALS | 22 ± 5 | 590 ± 45 | 1500 ± 730 | 630 ± 55 |
| | Total Streptomyces population (× $10^4$ CFU/g soil) | | | |
| Control | 64 ± 12 | 39 ± 7.2 | 290 ± 77 | 580 ± 21 |
| 0.5% ALS | 64 ± 12 | 14 ± 6.5 | 110 ± 28 | 130 ± 51 |
| 1.0% ALS | 64 ± 12 | 78 ± 71 | 120 ± 58 | 43 ± 5.7 |
| | Melanin-producing, non-sporulating Streptomyces population (× $10^3$ CFU/g soil) | | | |
| Control | 230 ± 52 | 46 ± 7 | 510 ± 500 | 660 ± 230 |
| 0.5% ALS | 230 ± 52 | 51 ± 22 | 10 ± 0 | 150 ± 56 |
| 1.0% ALS | 230 ± 52 | 160 ± 140 | 10 ± 0 | 77 ± 6 |

Effect of Ammonium Lignosulfonate on Soil Microbial Populations

Populations of total bacteria and Gram-positive were higher than control by 8 weeks after application of ammonium lignosulfonate (Table 2). Total bacterial counts were more than 10 fold greater than the control in 0.5% ammonium lignosulfonate treated soils. Bacterial populations in all treatments were generally the same by week 20.

By week 8 counts of Gram-negative bacteria were also higher in soils amended with ammonium lignosulfonate as compared to control soil (Table 2). Counts of Gram-negative bacteria in soils amended with 1.0% ammonium lignosulfonate were higher than with 0.5% ammonium lignosulfonate, particularly 8 weeks after addition of ammonium lignosulfonate (Table 2). At week 8 the number of Gram-negative bacteria in ammonium lignosulfonate treated plots were 10–100-fold greater than those of the control. By week 20, populations of Gram-negative bacteria found in soils amended with ammonium lignosulfonate dropped to levels similar to those found in control soils.

After an initial decline in numbers by week 8, populations of fluorescent bacteria in soil amended with 0.5% ammonium lignosulfonate remained at levels similar to those found in control Kitchen soil (Table 2). In soil amended with 1.0% ammonium lignosulfonate, numbers of fluorescent bacteria were similar to those found in control soil, except by week 20, in which numbers of fluorescent bacteria dropped to undetectable levels (Table 2).

Fungal populations were increased by the addition of 1.0/% ammonium lignosulfonate to soil on all sampling dates, reaching a population peak by week 14 in soils amended with 1.0% ammonium lignosulfonate (Table 2). Fungal populations in soils amended with 1.0% ammonium lignosulfonate were more than 10-fold greater than that of control soil. Fungal population peaks for both 0.5% and 1.0% ammonium lignosulfonate amended soils were similar in magnitude by week 14, dropping in both treatments by week 20 to levels still greater than those of control soil (Table 2).

Counts of total Streptomyces were reduced in soils amended with 0.5% ammonium lignosulfonate on all sampling dates as compared to the control (Table 2). In soils amended with 1.0% ammonium lignosulfonate, counts of Streptomyces were similar to those in unamended soil by week 8, then decreased in numbers to levels less than that found in control soil by week 20 (Table 2).

In our lab, we have developed a semi-selective medium for isolating Streptomyces from soil (Conn et al. 1998). On this medium, some Streptomyces spp. produce a melanoid pigment and do not sporulate. We have established that pathogenic Streptomyces bacteria are part of this group. In soils amended with either concentration of ammonium lignosulfonate, numbers of melanin-producing, non-sporulating Streptomyces were reduced to undetectable levels within 14 weeks after application (Table 2). By week 20, numbers of these Streptomyces returned to detectable levels, but were still reduced compared to numbers found in control soil (Table 2). Based on semi-selective medium, the potential number of pathogenic Streptomyces in 0.5% and 1% ammonium lignosulfonate treated soils were 10 to 100-fold lower than control soil.

Effect of Ammonium Lignosulfonate on Soil pH

Figure 7:
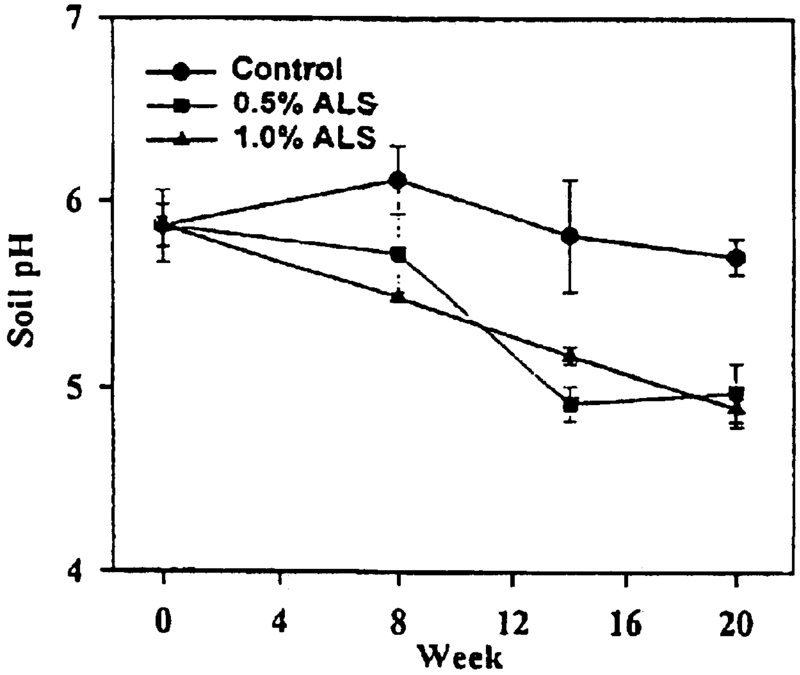
FIG. 7 is a graph of Example 3 illustrating the effect of ammonium lignosulfonate on soil pH.

Ammonium lignosulfonate caused a decrease in soil pH at both concentrations used (FIG. 7). In general, soil pH in ammonium lignosulfonate treated soils were 0.5–1 unit lower than untreated soil.

Effect of Ammonium Lignosulfonate on Weed Emergence

Figure 8:
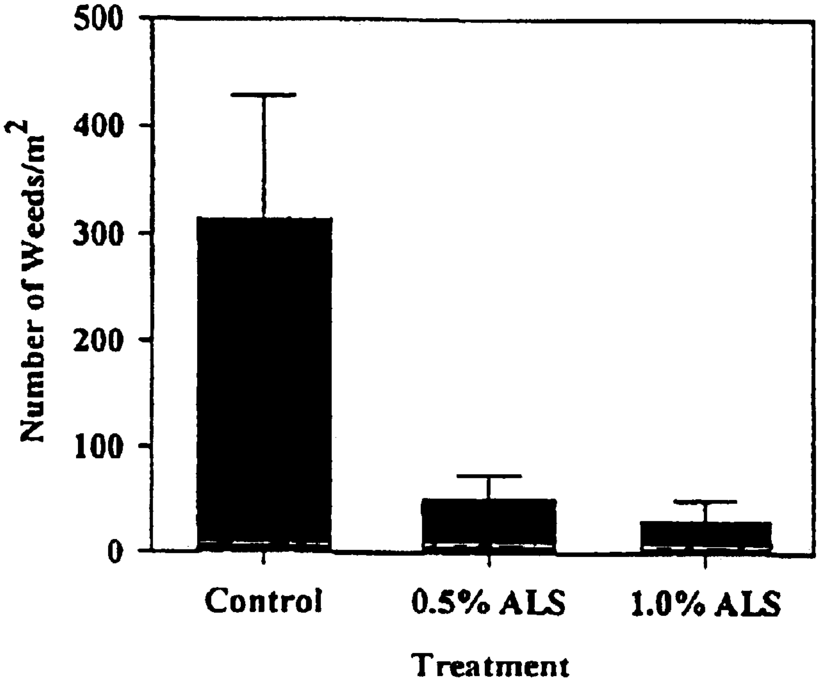
FIG. 8 is a graph of Example 3 illustrating the effect of ammonium lignosulfonate on weed populations in a commercial potato field.

Ammonium lignosulfonate significantly reduced the weed population at both concentrations and as compared to control (FIG. 8). Weed population in general was more than 6-fold lower in 0.5% ammonium lignosulfonate treated plots than control plots. Mean number of weeds was further decreased at 1.0% ammonium lignosulfonate treated plots. Direct phytoxicity and reduced light and moisture exposure are postulated to be the mechanisms by which ammonium lignosulfonate reduces weed population.

Effect of Ammonium Lignosulfonate on the Survival of *V. dahlie* Microsclerotia (MS)

Bags of *V. dahliae* MS were buried in the plots immediately after addition of ammonium lignosulfonate, removed 4 weeks later, and viability of MS determined. Both concentrations of ammonium lignosulfonate caused about 40% decrease in germination of *Verticillium dahliae* Microsclerotia (FIG. 8). Due to variability between replicate plots the results were not necessarily statistically significant.

Effect of Ammonium Lignosulfonate on the Incidence of Verticillium Wilt.

Figure 9:
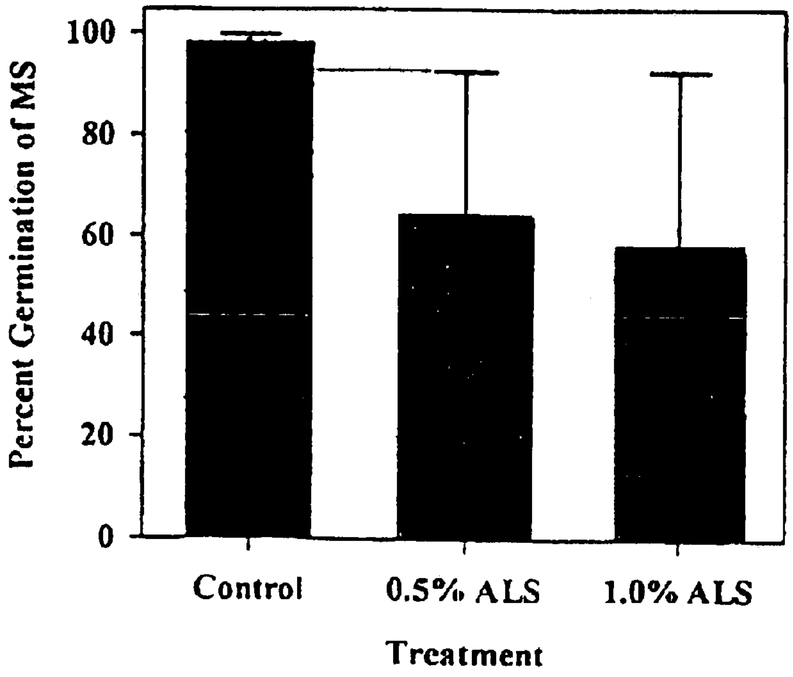
FIG. 9 is a graph of Example 3 showing the effect of ammonium lignosulfonate on the survival of *V. dahliae* microsclerotia in a commercial potato field.

Wilt incidence of potatoes was determined in August 1998. Both ammonium lignosulfonate concentrations caused a decrease in wilt incidence (FIG. 9). As the concentration of ammonium lignosulfonate was increased, the incidence of wilt decreased. Potato plants in control plots were 28% infected with Verticillium wilt while only 7% of plants in 1.0% ammonium lignosulfonate treated plots were infected (FIG. 9). However, these results were not necessarily statistically different due to variability between the replicate plots.

Effect of Ammonium Lignosulfonate on the Incidence of Potato Scab and Yield

Figure 10:
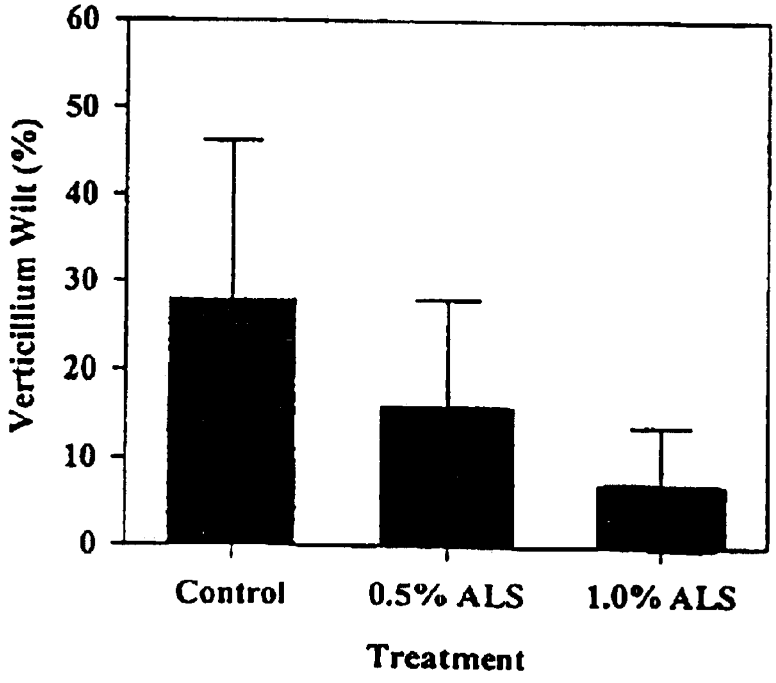
FIG. 10 is a graph of Example 3 showing the effect of ammonium lignosulfonate on the instance Verticillium wilt in a potato field.
Figure 12:
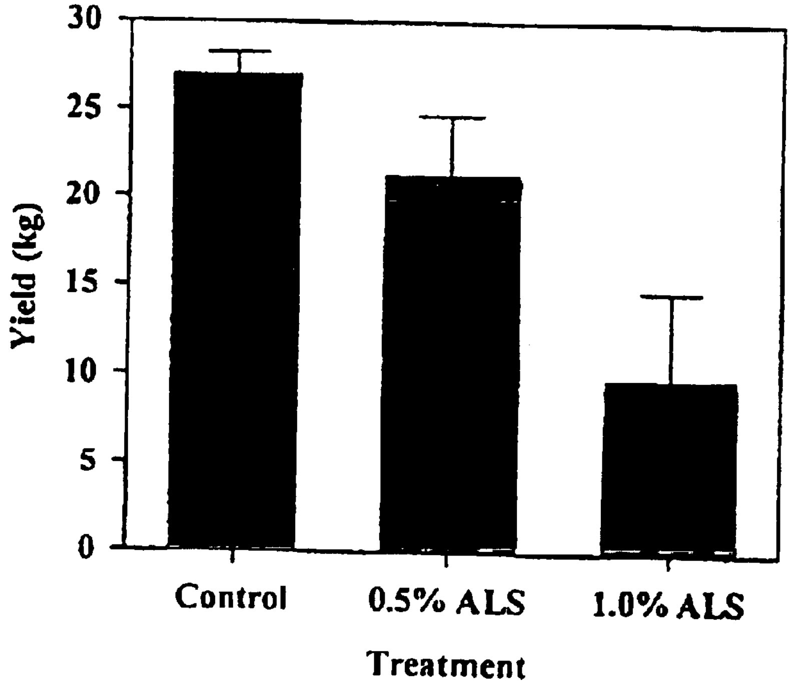
FIG. 12 is a graph of Example 3 illustrating the effect of ammonium lignosulfonate on the yield in a commercial potato field.
Figure 13:
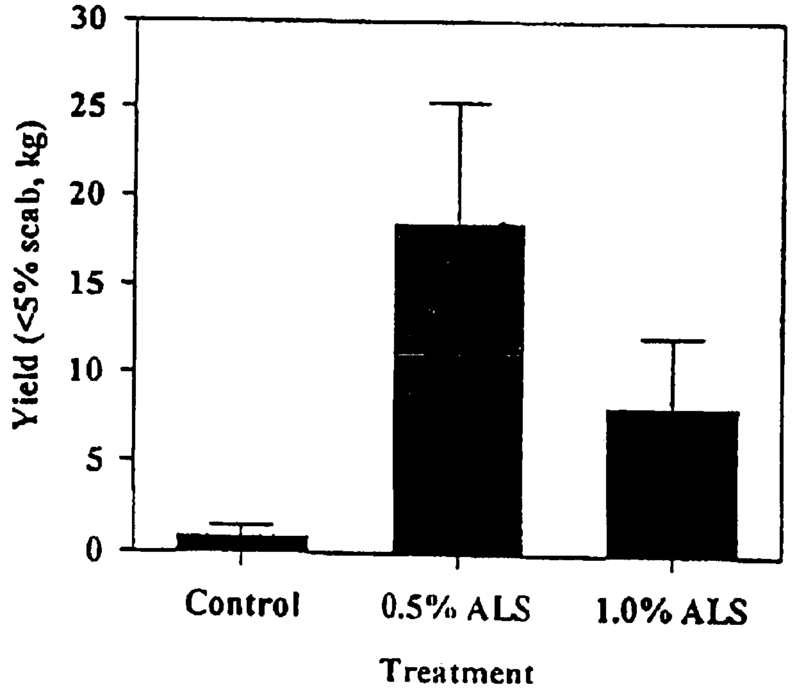
FIG. 13 is a graph of Example 3 showing the effect of ammonium lignosulfonate on the marketable yield in a commercial potato field.

Both concentrations of ammonium lignosulfonate caused a significant reduction in the incidence of potato scab as compared to the control (FIG. 10). There was no statistical difference between the ammonium lignosulfonate treatments. There was more tan 6-fold decrease in scab severity in 0.5% ammonium lignosulfonate treated plots than control plots. Total yield was slightly lower in ammonium lignosulfonate treated plots as compared to the control (FIG. 12). However, most of the tubers from the control plots were not marketable as they were severely infected with scab while those from ammonium polysulfonate treated plots had a scab severity index of less than one which made them marketable by the farmer (FIG. 13).

Figure 11:
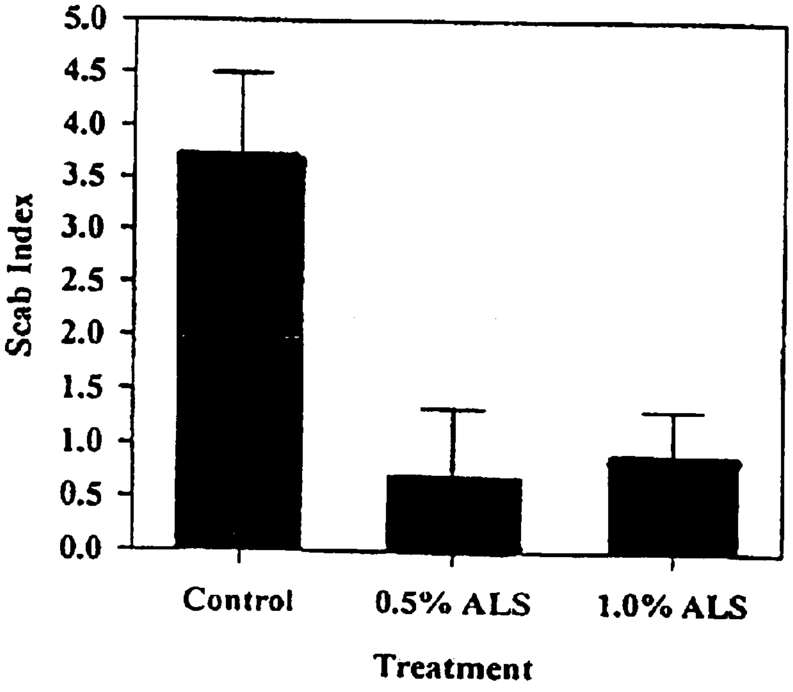
FIG. 11 is a graph of Example 3 showing the effect of ammonium lignosulfonate on the incidence of potato scab in a commercial potato field.
Figure 14:
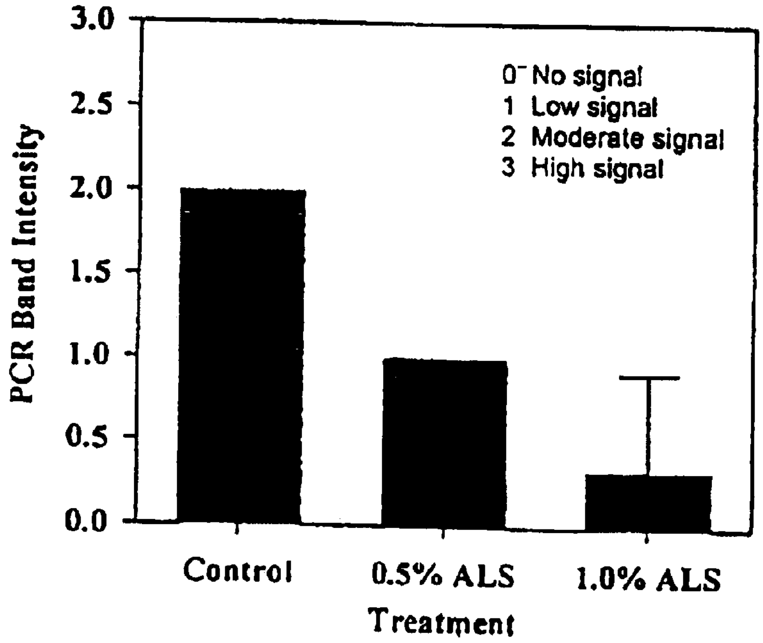
FIG. 14 is a graph of Example 3 of PCR intensity of bands collected from soil treated with ammonium lignosulfonate in a commercial potato field.

PCR Detection of Pathogenic Streptomyces spp. in Ammonium Lignosulfonate Treated Soils We used a technique recently developed in our lab to determine the population of pathogenic scab bacteria in soil samples taken at harvest time (week 20). Based on PCR band intensity results, the number of pathogenic scab bacteria in ammonium lignosulfonate treated soils were significantly lower than untreated soil (FIG. 14). These results are in agreement with our semi-selective medium counts (Table 2) and tuber potato scab index results (FIG. 11).

Example 4

An experimental plot was set up adjacent to experiment one on the same commercial potato farm near Delhi, Ontario in June, 1998. The quantities of ammonium lignosulfonate applied is listed in Table 3. Three replicate plots/treatment in a randomized block design were set up. Each plot was 15.5×100 ft.

TABLE 3

Amount of Ammonium Lignosulfonate (ALS)

| Treatments | Amount/plot[y] | Amount/acre | %/soil (v/w)[z] |
|---|---|---|---|
| 1. Untreated control | | | |
| 2. ALS | 25 gal (US) | 703 gal | 0.33% |

[y]Three replicate plots (15.5 × 100 ft)/treatment
[z]Based on the assumption that 1 $ft^2$ to a depth of 6 inches contains 40 lbs of soil.

The ammonium lignosulfonate was sprayed over the soil surface and then was rototilled with a rototiller to a depth of 6 inches. Fertilizer (nitrogen; 10.2%, potassium, 6.6%, phosphorous; 14.6%, calcium; 4.0%, magnesium; 3.2%, and zinc; 0.5%) at a rate of 1200 lbs/acre was broadcast on all plots, the plots were then cultivated twice, and potato tubers cv. Kennebec planted by the grower (5 rows of 100 plants/row). The plots were treated the same in all other ways. Soil samples were taken at 0, 4, and 12 weeks after amendment incorporation. About 20 soil cores to a depth of 6 inches were taken with a soil corer from each plot and mixed together. The effects of amendments on soil pH, and microbial populations were determined as described in Example 3. Incidence of Verticillium wilt and potato scab were determined as described in Example 3. Tubers were harvested in the fall from the middle 50 ft of the middle two rows of each plot and yield determined, potato scab was assessed as described in Example 3. The rest of the tubers were harvested and discarded and the grower cultivated the plots along with the rest of the field.

TABLE 4

Effect of Ammonium Lignosulfonate (ALS) (0.33% v/w) on microbial populations in a commercial farm

| Treatment | Weeks after application: 0 | 4 | 12 |
|---|---|---|---|
| Total bacterial population (× $10^4$ CFU/g soil) | | | |
| Control | 3400 ± 240 | 3800 ± 360 | 290 ± 6.7 |
| ALS | 3400 ± 240 | 15000 ± 1700 | 250 ± 70 |

TABLE 4-continued

Effect of Ammonium Lignosulfonate (ALS) (0.33% v/w) on microbial populations in a commercial farm

| Treatment | Weeks after application: 0 | 4 | 12 |
|---|---|---|---|
| Total Gram-negative bacterial population (× $10^3$ CFU/g soil) | | | |
| Control | 260 ± 93 | 68 ± 15 | 12 ± 4.9 |
| ALS | 260 ± 93 | 640 ± 160 | 8.4 ± 5 |
| Total Gram-positive bacterial population (× $10^4$ CFU/g soil) | | | |
| Control | 3400 ± 240 | 3800 ± 360 | 290 ± 6.5 |
| ALS | 3400 ± 240 | 15000 ± 1700 | 250 ± 70 |
| Fluorescent bacterial population (CFU/g soil) | | | |
| Control | 8500 ± 2900 | 800 ± 86 | 990 ± 280 |
| ALS | 8500 ± 2900 | 540 ± 270 | 40 ± 40 |
| Total fungal population (× $10^3$ CFU/g soil) | | | |
| Control | 390 ± 52 | 180 ± 14 | 57 ± 5.7 |
| ALS | 390 ± 52 | 3700 ± 920 | 180 ± 27 |
| Total Streptomyces population (× $10^3$ CFU/g soil) | | | |
| Control | 2700 ± 760 | 390 ± 75 | 82 ± 34 |
| ALS | 2700 ± 760 | 600 ± 32 | 60 ± 9.4 |
| Melanin-producing, non-sporulating Streptomyces population (× $10^3$ CFU/g soil) | | | |
| Control | 560 ± 190 | 46 ± 7 | 31 ± 6.1 |
| ALS | 560 ± 190 | 11 ± 0 | 3.7 ± 3.7 |

Effect of Ammonium Lignosulfonate on Soil Microbial Populations

Addition of 0.33% ammonium lignosulfonate caused an increase in the numbers of total bacteria by 4weeks after application after which numbers dropped to levels similar to those found in control soil (Table 4).

Counts of Gram-negative bacteria were higher in soil amended with ammonium lignosulfonate. By week 4, the population of Gram-negative bacteria in ammonium lignosulfonate treated soil was nearly 10-fold greater than control soil. By week 12, populations of Gram-negative bacteria found in soil amended with ammonium lignosulfonate dropped to levels similar to those found in control soils.

The population of Gram-positive bacteria generally had similar trends as those found for Gram-negative bacteria (Table 4). The population of Gram-positive bacteria increased by week 4 in ammonium lignosulfonate treated soil and then leveled to those of control soil by week 12.

Counts of fluorescent bacteria in soil amended with ammonium lignosulfonate declined to levels less than those found in unamended soil by week 12 (Table 4). At week 12, the population of fluorescent bacteria in ammonium lignosulfonate treated soils was more than 10-fold lower than control soil.

Total fungal counts were increased in soil amended with ammonium lignosulfonate as compared to the control soil reaching a population peak by week 4 (Table 4). After week 4, fungal counts declined but were still greater than those found in unamended soil by week 12.

Total Streptomyces were generally the same at all sampling weeks for both ammonium lignosulfonate amended and unamended soils (Table 4).

Counts of melanin producing, non-sporulating Streptomyces declined to undetectable levels by week 4 in soil amended with ammonium lignosulfonate (Table 4). Based on our semi-selective medium, the potential number of plant pathogenic Streptomyces was more than 10-fold lower in ammonium lignosulfonate treated soil than in control soil.

Effect of Ammonium Lignosulfonate on Soil pH

Figure 15:
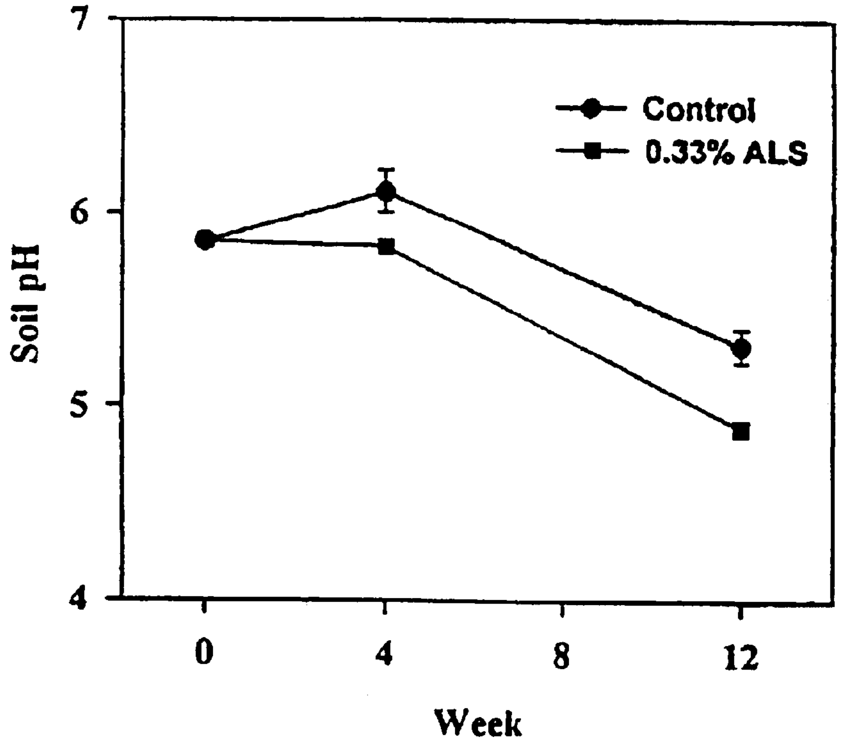
FIG. 15 is a graph from Example 4 showing the effect of ammonium lignosulfonate on soil pH in a commercial potato field.

Soil pH was lower in ammonium lignosulfonate treated soil at all sampling dates (FIG. 15). Soil pH gradually decreased during the growing season and was nearly 0.5 unit lower in ammonium lignosulfonate treated soils than control soils at week 12.

Effect of Ammonium Lignosulfonate on the Incidence of Verticillium Wilt.

Figure 16:
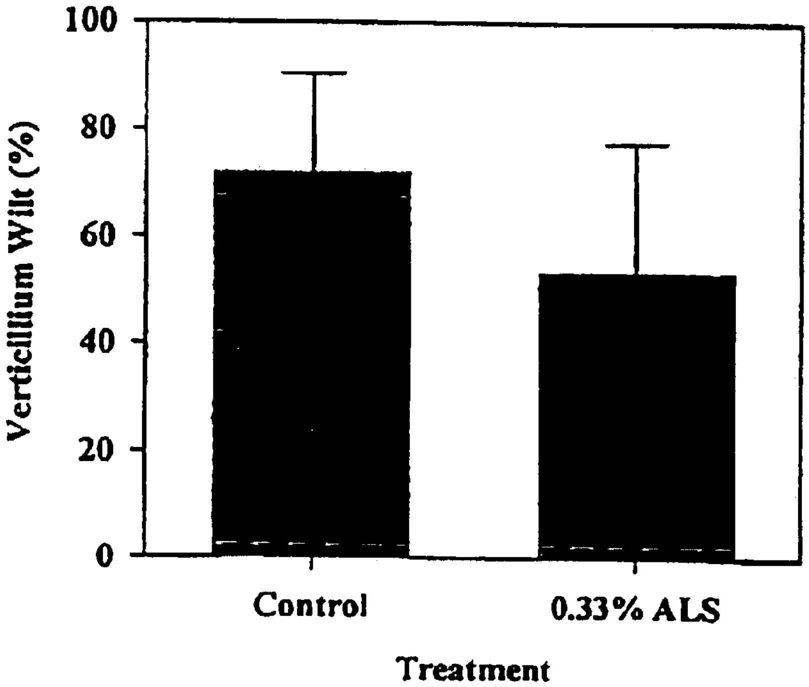
FIG. 16 is a graph from Example 4 showing the effect of ammonium lignosulfonate on the incidence of Verticillium wilt in a commercial potato field.

Wilt incidence of potatoes was determined in August 1998. Plots treated with ammonium lignosulfonate had decreased wilt incidence (FIG. 16). Potato plants in control plots were 72% infected with Verticillium wilt while only 53% of plants in ammonium lignosulfonate treated plots were infected. However, these results were not statistically different due to variability between the replicate plots.

Effect of Ammonium Lignosulfonate on the Incidence of Potato Scab and Yield

Figure 17:
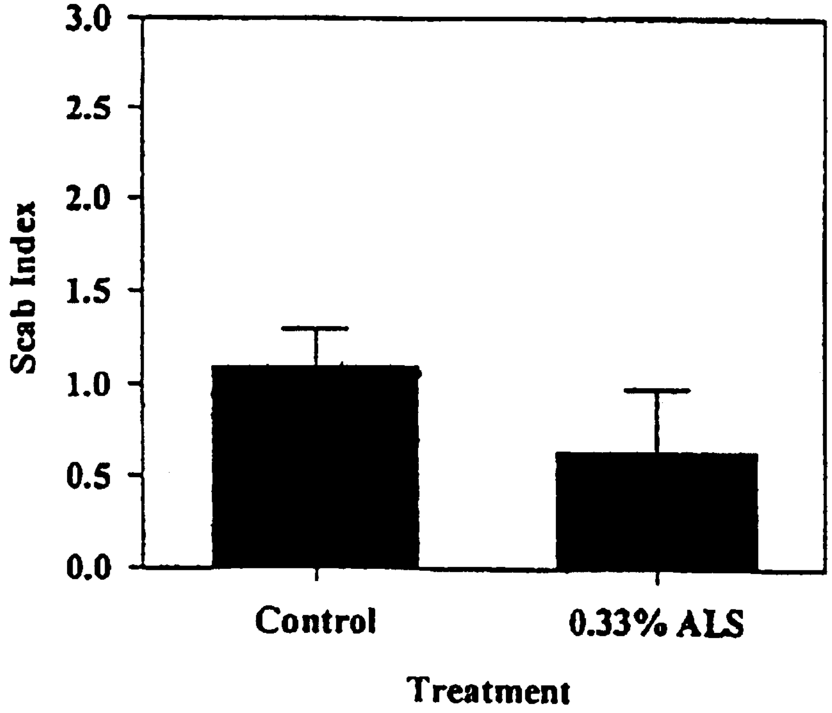
FIG. 17 is a graph from Example 4 showing the effect of ammonium lignosulfonate on the incidence of potato scab in a commercial potato field.

Soils treated with ammonium lignosulfonate had reduced incidence of potato scab (FIG. 17). Mean scab index for ammonium lignosulfonate treated soils was 0.64 while the untreated soils had a mean scab index of 1.1.

Figure 18:
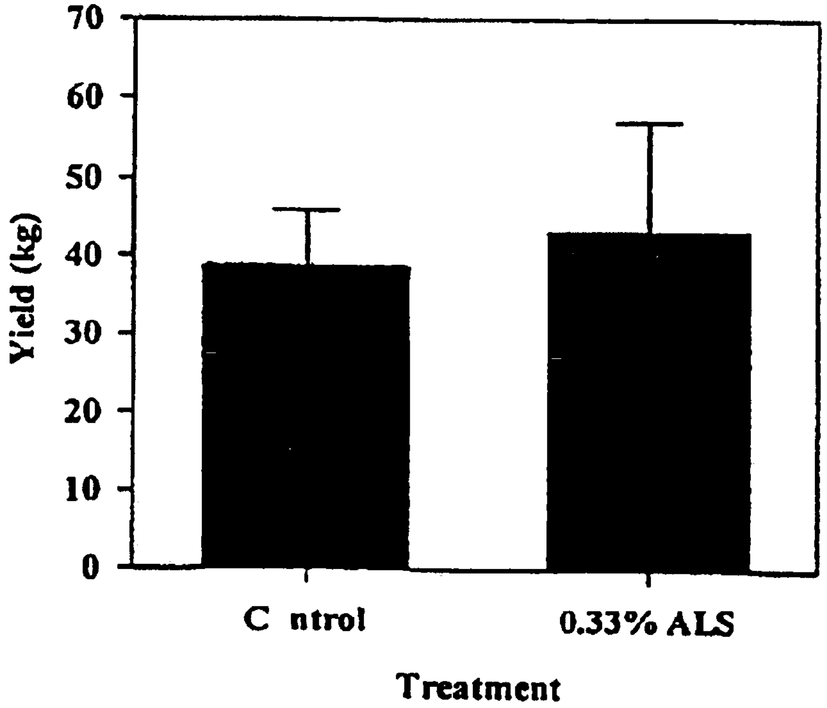
FIG. 18 is a graph from Example 4 showing the effect of ammonium lignosulfonate on the yield in a commercial potato field.
Figure 19:
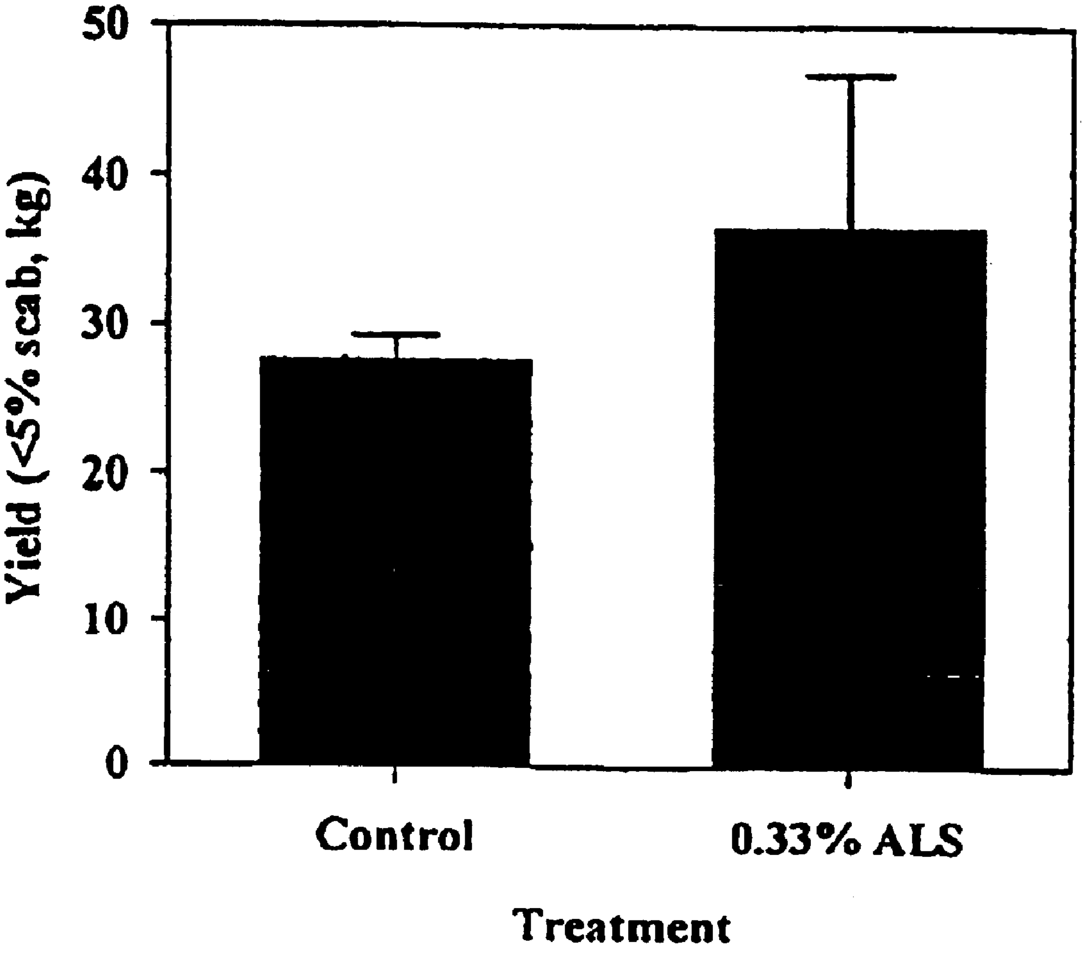
FIG. 19 is a graph from Example 4 showing the effect of ammonium lignosulfonate on the marketable yield in a commercial potato field.

Total yield was 43.3 kg and 38.7 kg for ammonium lignosulfonate and control treatments respectively (FIG. 18). There were 30% more marketable tubers in ammonium lignosulfonate treated plots than the control plots (FIG. 19). There were no statistical differences due to variability between the replicate plots.

Results from the above experiments showed that incorporation of ammonium lignosulfonate into soil caused an increase in most microbial populations. Most of these populations gradually returned to control levels by the end of season except for the fungal population that remained higher than control. Ammonium lignosulfonate caused a decrease in viability of *V. dahliae* microsclerotia and reduced the incidence of Verticillium wilt. Populations of pathogenic scab bacteria were reduced after application of ammonium lignosulfonate and the incidence of potato scab was reduced in all ammonium lignosulfonate treated plots. Marketable tuber yield was increased in all ammonium lignosulfonate treatments in both experiments.

Thus, we have shown that addition of ammonium lignosulfonate to soil reduced populations of important fungal and bacterial soil borne pathogens, while increasing the overall microbial population by 10 to 100-fold. This is unlike chemical fumigants which reduce the populations of all soil microorganisms, both good and bad species. Often, soil borne bacterial and fungal pathogens return to even higher levels than before the fumigation because of the lack of competition from other microorganisms. Ammonium lignosulfonate thus becomes a component for plant disease control and an alternative to fumigants for the control of bacterial and fungal soil borne plant pathogens. At the higher concentrations used, ammonium lignosulfonate had a phytotoxic effect on potatoes. This phytotoxicity, however, was transitory at rates below 0.5% and the plants recovered and caught up to the plants in untreated soil.

As used herein, when reference is made to a volume/weight basis, it is assumed that the soil weight of 1 square meter to a depth of 15 centimeters is approximately 200 kilograms. Therefore, 0.5% ALS equals 5.0 ml/Ag ×200= 1000 ml ALS/$m^2$.

What is claimed is:

1. A method of controlling at least one soil pathogen selected from the group consisting of *verticillium dahliae*, Streptomyces, Phylophthora, Pythium, Rhizoctonia, and Sclerotinia contained in a soil comprising applying and incorporating into said soil containing at least one of said soil pathogens an amount of a composition consisting essentially of a lignosulfonate that is effective to reduce the population of said at least one soil pathogen, wherein effective population reduction of said soil pathogen is obtained from the lignosulfonate, the effective amount of the composition is 0.05 to 5% volume of the composition based on weight of the soil, and the incorporation of the composition into the soil provides an increase in beneficial soil microbial population.

2. The method of claim 1, wherein the lignosulfonate is ammonium lignosulfonate.

3. The method of claim 2, wherein said ammonium lignosulfonate is applied to a surface of said soil and said ammonium lignosulfonate is incorporated into said soil.

4. The method of claim 2, wherein the composition is applied and incorporated into said soil in an amount between about 0.1 to 2% volume of the composition based on weight of the soil.

5. The method of claim 4, wherein the composition is applied as a liquid.

6. A method of treating potato scab disease caused by bacteria Streptomyces comprising applying and incorporating into a soil containing potatoes and said bacteria an amount of a composition consisting essentially of ammonium lignosulfonate that is effective to reduce the population of said bacteria, wherein effective population reduction of said bacteria is obtained from the ammonium lignosulfonate, the effective amount of the composition is 0.05 to 5% volume of the composition based on weight of the soil, and the incorporation of the composition into the soil provides an increase in beneficial soil microbial population.

7. The method of claim 6, wherein the composition is applied and incorporated in an amount of between 0.1 to 2% volume of the composition based on weight of the soil.

8. A method of controlling at least one soil pathogen selected from the group consisting of *verticillium dahliae*, Streptomyces, Phylophthora, Pythium, Rhizoctonia, and Sclerotinia contained in a soil wherein potatoes are to be planted comprising applying and incorporating into said soil containing at least one of said soil pathogens an amount of a composition consisting essentially of a lignosulfonate that is effective to reduce the population of said at least one soil pathogen, wherein effective population reduction of said soil pathogen is obtained from the lignosulfonate, the effective amount of the composition is 0.05 to 5% volume of the composition based on weight of the soil, and the incorporation of the composition into the soil provides an increase in beneficial soil microbial population.

9. The method of claim 8, wherein the lignosulfonate is ammonium lignosulfonate and the composition is applied and incorporated in an amount of between 0.1 and 5% volume of the composition based on weight of the soil.

* * * * *